US008998816B2

(12) United States Patent
Kassab et al.

(10) Patent No.: US 8,998,816 B2
(45) Date of Patent: *Apr. 7, 2015

(54) DEVICES, SYSTEMS AND METHODS FOR ISOMETRIC AND ISOTONIC CONTRACTION OF BLOOD VESSELS USING AN ISOVOLUMETRIC MYOGRAPH

(75) Inventors: Ghassan S. Kassab, Newport Coast, CA (US); Xiao Lu, Irvine, CA (US)

(73) Assignee: DTherapeutics, LLC, San Diego, CA (US)

( * ) Notice: Subject to any disclaimer, the term of this patent is extended or adjusted under 35 U.S.C. 154(b) by 1602 days.

This patent is subject to a terminal disclaimer.

(21) Appl. No.: 11/919,469

(22) PCT Filed: May 1, 2006

(86) PCT No.: PCT/US2006/016523
§ 371 (c)(1),
(2), (4) Date: Oct. 29, 2007

(87) PCT Pub. No.: WO2006/119143
PCT Pub. Date: Nov. 9, 2006

(65) Prior Publication Data
US 2009/0023176 A1    Jan. 22, 2009

Related U.S. Application Data

(60) Provisional application No. 60/675,908, filed on Apr. 29, 2005.

(51) Int. Cl.
*A61B 5/02*    (2006.01)
*G01N 33/49*    (2006.01)
*A61B 5/021*    (2006.01)

(52) U.S. Cl.
CPC ............... *G01N 33/49* (2013.01); *A61B 5/021* (2013.01)

(58) Field of Classification Search
CPC ............... G01N 33/49; A61B 2503/40; A61B 5/02007; A61B 5/036; A61B 5/04882; A61B 5/418
USPC .............................. 600/36; 435/395, 404, 405
See application file for complete search history.

(56) References Cited

U.S. PATENT DOCUMENTS

| | | | | |
|---|---|---|---|---|
| 4,000,742 | A * | 1/1977 | Digicomo | 604/83 |
| 2003/0097040 | A1* | 5/2003 | Clerin et al. | 600/36 |
| 2003/0100824 | A1* | 5/2003 | Warren et al. | 600/407 |
| 2003/0135237 | A1* | 7/2003 | Cragg et al. | 606/213 |

(Continued)

OTHER PUBLICATIONS

VanBavel et al. "Cannulation and Continuous Cross-sectional Area Measurement of Small Blood Vessels," Nov. 1, 1990, Journal of Pharmacological Methods, vol. 24, No. 3: 219-227.*

(Continued)

*Primary Examiner* — Navin Natnithithadha
*Assistant Examiner* — Eric Messersmith
(74) *Attorney, Agent, or Firm* — Reichel Stohry LLP; Mark C. Reichel; Natalie J. Dean (57) ABSTRACT

The present invention discloses devices, systems and methods for the isovolumic measurement of vasoactivity in a blood vessel (3). The length and volume of the blood vessel (3) are maintained constant while a chemical or pressure is exposed to the blood vessel (3). The reaction of the blood vessel (3) to the chemical or physical stimuli is measured by internal lumen pressure changes.

24 Claims, 8 Drawing Sheets

(56) References Cited

U.S. PATENT DOCUMENTS

2006/0078265 A1* 4/2006 Loeb ............................ 385/141
2009/0123993 A1* 5/2009 Banes et al. ............... 435/284.1

OTHER PUBLICATIONS

Ohtaka et al. "Mechanical properties of porcine intralobar pulmonary arteries," Apr. 1, 1988, Journal of Applied Physiology, vol. 64, No. 4: 1537-1545.*

Mulvany and Halpern. "Contractile Properties of Small Aterial Resistance Vessels in Spontaneously Hypertensive and Normotensive Rats" Jul. 1977, vol. 41, No. 1:19-26.*

"Single Vessel Chambers" Living Systems Instrumentation. Retrieved from the Internet. <URL: http://web.archive.org/web/20031206180755/http://livingsys.com/singlechambers.htm> Published Dec. 6, 2003. Retrieved on Jun. 16, 2011. 1-3.*

Falloon, B,J, and Heagerty, A.M., In Vitro Perfusion Studies of Human Resistance Artery Function in Essential Hypertension, Hypertension, vol. 24, pp. 16-23, 1994.

Ohtaka, H. et al., Mechanical Properties of Porcine Intralobar Pulmonary Arteries, Journal of Applied Physiology, vol. 64, No. 4, pp. 1537-1545, Apr. 1, 1988.

Vanbavel, E. et al., Cannulation and Continuous Cross-sectional Area Measurement of Small Blood Vessels, Journal of Pharmacological Methods, vol. 24, No. 3, pp. 219-227, 1990.

European Search Report, European Patent Office, European Application Serial No. 06751942.1, dated Nov. 17, 2009.

Supplementary European Search Report, European Patent Office, European Application Serial No. 06751942.1, dated Nov. 6, 2009.

Mulvany, M.J., Contractile properties of small arterial resistance vessels in spontaneously hypertensive and normotensive rats, Circulation Research, Jul. 1977, vol. 41, No. 1, pp. 19-26.

International Searching Authority, International Search Report, Nov. 30, 2006.

International Searching Authority, Written Opinion of the International Searching Authority, Nov. 30, 2006.

* cited by examiner

DEVICES, SYSTEMS AND METHODS FOR ISOMETRIC AND ISOTONIC CONTRACTION OF BLOOD VESSELS USING AN ISOVOLUMETRIC MYOGRAPH

RELATED APPLICATIONS

The present application is a U.S. National Stage Application of International Patent Application Serial No. PCT/US2006/016523, filed May 1, 2006, the contents of which are herein incorporated by reference, which claims priority to U.S. Provisional Patent Application Ser. No. 60/675,908, filed Apr. 29, 2005, the content of which is hereby incorporated by reference.

BACKGROUND OF THE INVENTION

1. Field of the Invention

The present invention relates to the measurement of isometric and isotonic contraction of blood vessels. More particularly, the present invention relates to devices, systems and methods for isometric and isotonic contraction of blood vessels using an isovolumic myograph.

2. Background of the Invention

Vascular smooth muscle coils (VSMCs) modulate the tone of a blood vessel in response to neural, humoral or local hemodynamic stimuli. The VSMCs are important for autoregulation and largely determine the spatial and temporal distribution of blood flow in an organ. Thus, conditions that affect the proper function of VSMCs cause a variety of medical problems.

Many diseases, including hypertension, diabetes, heart failure and atherogenesis, show signs of impaired arterial vasoactivity. Hypertension, for example, is identified in relation to changes in the myogenic tone of the resistance arteries. The vasoactivity may be attenuated due to physiological (normal growth, exercise, pregnancy, etc.) or pathological remodeling (hypertension, hypertrophy, heart failure, etc.). The pressure-induced myogenic response (or tone) is initiated as a consequence of pressure-dependent modification of vascular smooth muscle wall tension and subsequent activation of mechanosensitive ion channels. Steady-state myogenic tone accounts for a substantial portion of the peripheral resistance and is an important determinant of arterial blood pressure. Although vasoconstriction and vasodilation are intrinsic properties of VSMC, they are often modulated by endothelium-derived vasoactive factors.

Because of the importance of maintaining proper vasoactivity in VSMC, various drugs are tested for their effects on such vasoactivity. Two of the tools used in such tests to identify vasoactivity in blood vessels include the wire and pressure myographs. A Medline search with keyword "wire myograph" or "pressure myograph" reveals 140 and 207 publications, respectively, from 1990 to the present having at least some reference to these conventional tools for testing vasoactivity. In pharmacology, these methods are used to understand the vasoreactivity and the dose-response relation of various agonists and antagonists.

Although the wire myograph method is used often for pharmacological experiments, it has a number of drawbacks, one being that it is far from physiological. The mechanical deformation of the ring is non-physiological and the cutting of the vessel produces some injury to the vessel which has a direct impact on the response of the vessel to the testing.

The pressure myograph was developed to address some of the limitations of the wire myograph. In the pressure myograph, the vessel geometry and loading are typically more physiological. The pressure myograph method involves changes in pressure while recording the change in diameter under passive and active conditions. The method is substantially isobaric because the pressure is maintained constant during contraction. Since the radius changes during the test, which can change the wall stress (based on Laplace's equation), this method of mechanical testing is neither isometric nor isotonic, which in turn affects interpretation of the results.

Thus, although both of the above conventional methods are widely in use, a need exists in the art for an alternative to the conventional techniques for testing vasoactivity in blood vessels such that the need addresses the setbacks and limitations of the conventional techniques, while at the same time, is easy to use and interpret and provides a more accurate measurement of vasoactivity.

SUMMARY OF THE INVENTION

The present invention presents a novel isovolumic myograph which maintains substantially constant dimensions of a blood vessel while recording the changes in pressure in response to vasoconstrictors or vasodilators. In essence, the present invention has the advantages of the other two conventional myographs, by being both isometric and isovolumic, without the disadvantages. To demonstrate the utility and sensitivity of the new technique, a response of elastic (carotid) and muscular (femoral) arteries is considered. Evidence shows that the present invention is sensitive to the response of both types of vessels. Characteristic curves for the passive and active response of the two vessel types are presented. The usefulness of this novel technique and future applications to physiology and pharmacology are limitless.

In one particular embodiment of the present invention, a device is disclosed for determining the vasoactivity of a blood vessel. The device includes a pair of conduits positioned at either end of a blood vessel, wherein each conduit forms a fluid seal with the lumen of the blood vessel; a pair of retaining walls that retain the blood vessel in a predetermined length; a pressure transducer in communication with one of the conduits; and wherein any vasoactivity of the blood vessel is influenced by pressure fluctuations in the lumen of the blood vessel as measured by the pressure transducer while the blood vessel is maintained in the predetermined length by the retaining walls.

In another exemplary embodiment, the present invention is a system for determining the vasoactivity of a blood vessel in reaction to a chemical. The system includes a blood vessel used to determine the vasoactivity of a chemical; wherein the lumen of the blood vessel is closed to flow conditions such that the blood vessel is maintained at constant volume; a retaining device that retains the blood vessel in a predetermined length; a chemical used to test the vasoactivity of the blood vessel; and wherein any vasoactivity of the blood vessel in response to the chemical is measured in an isovolumic and isometric state.

In yet another exemplary embodiment, the present invention is a method for measuring the vasoactivity of a blood vessel in response to a chemical. The method includes maintaining the blood vessel at a constant length; maintaining the blood vessel at a constant internal volume; and measuring pressure changes inside the lumen of the blood vessel after exposure of the blood vessel to the chemical.

DETAILED DESCRIPTION OF THE INVENTION

To understand and fully appreciate the advantages of the present invention, it is useful to first consider the conventional techniques that are in use today, their uses and their drawbacks, and consider an engineering analysis that leads to the present invention.

Conventionally, wire and pressure myographs are widely used to study the vasoactive properties of blood vessels. In the wire myograph, the blood vessel is cut into rings and each ring is mounted by two hooks in an isometric myograph. Typically, one of the hooks is fixed while the other is connected to a force transducer. The length of the ring is maintained relatively constant (isometric) while the measured force is recorded during vasoconstriction or vasodilatation. A useful property of this model is that it tests isometric properties with high sensitivity but some drawbacks include the non-physiological nature of the blood vessel geometry and the mechanical loading. To remedy these drawbacks, the pressure myograph was developed.

In the pressure myograph, the blood vessel is cannulated to a perfusion system and connected to a pressurized container which can regulate the pressure. A microscope with a CCD camera is used to monitor the diameter of the vessel. The increase or decrease of the diameter reveals the vasodilatation or vasoconstriction, respectively. In comparison with the isometric wire myograph, the measurement in the pressure myograph is more physiological.

However, the sensitivity to detect vasoactivity in the pressure myograph is lower than in the wire myograph. In other words, the force change is much larger than the diameter change in the blood vessel during vasoactivity, especially for elastic vessels. For example, the force in the isometric myograph may increase many fold during norepinephrine-induced vasoconstriction. At similar conditions, the diameter changes about 10-20% in a pressure myograph. The force in an isometric myograph may decrease to zero during acetylcholine-induced vasodilatation while the dimension changes less than 10% in a pressure myograph. Such discrepancies and variations are just some of the drawbacks of these conventional systems and must be kept in mind when considering the following engineering analysis of the reaction of blood vessels in the body to determine an improved technique of measuring vasoactivity.

Under homeostatic in vivo conditions, blood vessels are arguably under more isometric than isotonic conditions. This is supported by the observation that the variation in vessel diameter is less than 10% during the cardiac cycle while the mean hoop stress ($\tau_\theta$) which can be estimated as the product of pressure (P) and inner radius ($r_i$) divided by the wall thickness (h) varies much more than that. This follows from Laplace's equation which can be stated as $$\tau_\theta = \frac{P r_i}{h} \qquad [1]$$

The inner radius and wall thickness are related, however, through the incompressibility principle which can be given as $$A_0 L_0 = \pi(r_o^2 - r_i^2)L = \pi h(r_0 - r_i)L \qquad [2a]$$

where $A_0$ and $L_0$ correspond to the wall area and length of vessel in the no-load state (zero-transmural pressure) and $r_o$ and L correspond to the outer radius and length of vessel in the loaded state. Approximating the vessel as thin walled; i.e., $r_o \sim r_i$, equation [2a] becomes $$h = \frac{A_0}{2\pi \lambda_z r_i} \qquad [2b]$$

where $\lambda_z$ is the axial stretch ratio given by $L/L_0$ and $h = r_o - r_i$. If equations [1] and [2b] are combined, the following equation is obtained $$\tau_\theta = \frac{2\pi \lambda_z}{A_0} P r_i^2 \qquad [3]$$

Since both pressure and radius change throughout the cardiac cycle, the change in stress will be much larger than the change in radius as shown by equation [3]. Thus, the vessel experiences more isometric than isotonic conditions in vivo.

Furthermore, the computation of tension or stress for the cylindrical geometry using Laplace's equation requires that the vessel be under equilibrium conditions. This occurs under isometric not isotonic conditions. For these reasons, the present invention was devised to allow the determination of active mechanical properties of blood vessels under isometric conditions while preserving the physiological geometry and pressure loading.

The isovolumic myograph according to the present invention has the advantages of both wire and pressure myographs while avoiding their limitations. In the isovolumic myograph, the blood vessel is cannulated and distended similarly to a pressure myograph and the vasoconstriction or vasodilatation response is determined through pressure signals. Using the exemplary embodiments of the present invention, very small pressure changes can be measured in a similar manner as the wire myograph while maintaining a physiological geometry and loading of the blood vessel similar to the pressure myograph.

Furthermore, a method according to the present invention is used to show that the pressure during vasoconstriction may increase up to 3-fold or higher depending on the initial pressure. Similarly, vasodilatation induces a significant pressure drop, as much as from 80 mmHg to 0 mmHg when the vessel was pre-constricted by Phenylephrine.

Figure 1:
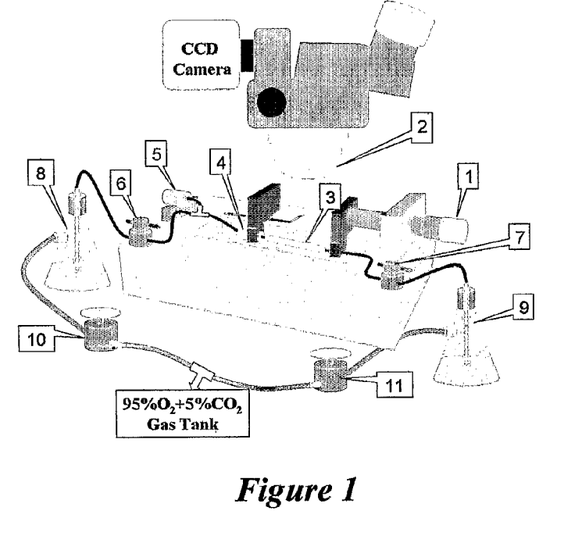
FIG. 1 shows an exemplary embodiment of the present invention as an isovolumic myograph in the process of testing a blood vessel.

In one particular exemplary embodiment of the present invention, an isovolumic myograph system is disclosed as shown in FIG. 1. A stereomicroscope 2 is used to detect and measure the changes in dimensions and geometry of a blood vessel 3 under consideration. A micromanipulator 1 allows the length of the blood vessel 3 to be properly positioned within the unit and connected to an axial force transducer 4. A constant and/or continuous volume is maintained through the closed unit, controllable by stopcocks 6 and 7 positioned in close proximity to either end of the blood vessel, and adjacent to flasks 8 and 9, respectively. Pressure regulators 10 and 11 are used to set and control the gas pressure within the closed fluid path which in turn controls the pressure within the lumen of blood vessel 3 while solid-state pressure transducer 5 detects such pressure of the fluid within the lumen of blood vessel 3.

Figure 5A:
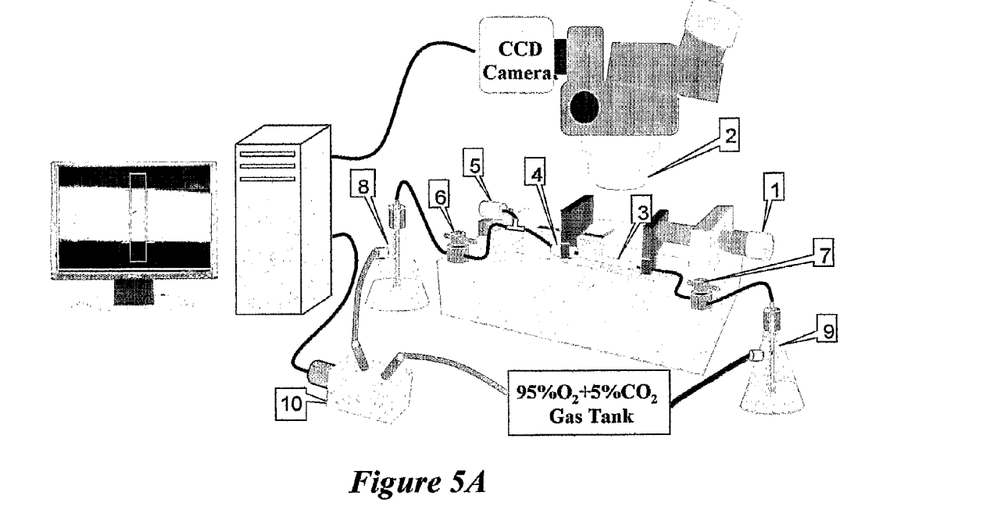
FIG. 5A shows an exemplary embodiment of the present invention as an automated isometric or isotonic myograph in the process of testing a blood vessel.

In operation, the exemplary isovolumic myograph in FIG. 1 serves to maintain an isovolumic environment for the blood vessel 3 under consideration of and exposure to a particular drug, agonist, or the like. The various components shown in FIG. 1 serve to allow the introduction of fluid into the lumen of the blood vessel, or alternatively, allow the constant flow of fluid through the blood vessel. Using either method, the dimensions and stresses on the blood vessel 3 is measured using the pressure transducer 5 and microscope 2 and recorded through a camera and recording system for later analysis. Alternatively, and as shown in FIG. 5A, a computer system may be in real-time communication with the microscope 2 and camera system such that the measurements and stresses of the blood vessel 3 are presented in a display in real time.

To consider the measurements and analysis of the exemplary embodiment of the present invention as shown in FIG. 1, an experiment was conducted using arterial segments from rats. Six Wistar rats weighing 300-350 g were used in the study. The animals were anesthetized with sodium pentobarbital (60 mg/kg, ip). A heating pad was used to maintain the body temperature of the animal during anesthesia. The left carotid and common femoral arteries of the rat were exposed and cannulated for blood pressure measurements. This was done to measure the in vivo difference in blood pressure between carotid and femoral arteries. Several 1 cm segments of right carotid and femoral arteries were excised and immediately stored in 4° C. physiological saline solution (PSS).

The samples were then prepared to be tested in the exemplary isovolumic myograph according to the present invention as shown in FIG. 1. To prepare the samples, PSS was first contained in an organ bath with a controlled heating system and warmed to 37° C. The PPS in the organ bath was aerated by a mixture of 95% $O_2$ and 5% $CO_2$ throughout the experiment.

A micromanipulator 1 was mounted on the edge of organ bath as shown in FIG. 1. An "arm" fixed on the micromanipulator 1 was used to hold a connector to a cannulate on one end of blood vessel 3, and a second arm held a connector to cannulate on the other end of the blood vessel 3. Both connectors were immersed into PSS in the organ bath and the vessel 3 was cannulated on the two ends. The back ends of the two connectors were connected with thick-wall Tygon tubing to individual two-way stopcocks 6 and 7. A solid-state pressure transducer 5 was inserted into the tubing between the connector and a two-way stopcock 6 to monitor the pressure in the blood vessel 3. Each two-way stopcock 6 and 7 was connected to an individual flask (approximately 50 ml) 8 and 9, respectively, with about 20 ml of PSS or some agonist to fill the blood vessel lumen. Each flask 8 and 9 was pressurized by a mixed 95% $O_2$ and 5% $CO_2$ gas tank and the pressure in each flask was regulated by an independent pressure regulator 10 or 11. The regulator 10 or 11 pressurizes the fluid in the flask 8 or 9, respectively, to any desired pressure (the accuracy being to within about 1 mmHg).

The blood vessel 3 and pressure transducer 5 are isolated from the pressure system when the vessel 3 is pressurized and the two stopcocks 6 and 7 are closed to the vessel 3. Since the two ends of the vessel 3 are closed off, the vessel contraction causes an increase in intravascular pressure. During vasodilatation, the vessel 3 expands, and hence results in a decrease of intravascular pressure. The changes of the pressure are recorded. The diameter change, however, is very small in the isovolumic system as confirmed by a CCD camera mounted on a stereomicroscope 2 to record the diameter change. Pharmacological agonists may be endothelium-dependent and hence could be introduced through the lumen, or may be endothelium-independent and hence could be applied externally to the vessel 3 in the bath.

With the aid of stereomicroscope 2, the adjacent loose tissue of the vessel 3 was dissected carefully and all of the branches of the vessel 3 were ligated by suitable suture in 4° C. PSS. The vessel 3 was then cannulated onto the connectors in the organ bath containing PSS in room temperature and gassed by 95% $O_2$/5% $CO_2$ at 37° C. The vessel 3 was stretched to its in vivo length and the two stopcocks 6 and 7 were opened to the vessel 3. The intravascular pressure was set at 10 mmHg to allow the vessel 3 to equilibrate for 40 minutes. The intravascular pressure was then increased to 60 mmHg and the two stopcocks 6 and 7 were simultaneously closed to the vessel 3. The vessel 3 was challenged twice by phenylephrine at 1 μmole/L. The PSS was replaced and the vessel 3 was allowed to equilibrate for 40 min. The vessel 3 segment was then pressurized to 100 mmHg in the carotid artery while the femoral artery was pressurized to 85 mmHg.

The dosage-dependent vasoconstriction in response to phenylephrine was recorded. The dosage- and endothelium-dependent vasodilatation in response to acetylcholine was also recorded in phenylephrine pre-constriction. The dosage-dependent and endothelium-independent vasodilatation in response to sodium nitroprusside (SNP) was recorded in phenylephrine pre-constriction. The maximum concentrations of agonists were then used in the pressure-dependent myogenic contraction which induced maximum vasoconstriction and vasodilation as outlined below.

The vessel was pressurized at 10 mmHg for 5 minutes and the two stopcocks 6 and 7 were closed simultaneously. The PSS with maximum concentration of phenylephrine caused vasoconstriction compared to the PSS in the organ. The pressure in the vessel 3 and diameter of the vessel 3 were recorded. The PSS with phenylephrine was drained and PSS was refilled into the organ bath. Vessel 3 was allowed to recover for 40 minutes and was then pressurized from 20 to 140 mmHg in increments of 20 mmHg. At every pressure, vasoconstriction induced by phenylephrine was repeated as outlined above. The vessel 3 was then allowed to recover for 40 minutes between every phenylephrine administration.

After the vasoactivity experiment, calcium-free PSS with 2.5 mmole/L EGTA was used to replace the PSS in the organ bath and flasks 8 and 9. After 20 minutes, the diameter of the vessel 3 was recorded at every setting pressure: 10, 20, 40, 60, 80, 100, 120, 140, and 160 mmHg. The vessel 3 was disconnected from the organ bath and three rings (0.5 mm length) were cut from the vessel 3. The cross-section was videotaped and wall area and inner and outer perimeters were measured. The rings were further cut radially and the inner and outer lengths were measured at zero-stress state.

PSS used in these experiments was made of (in mmole/L): 119 NaCl, 4.7 KCl, 25 $NaHCO_3$, 1.17 $KH_2PO_4$, 1.17 $MgSO_4$, 1.6 CaCl, 5.5 Glucose. Phenylephrine and acetylcholine were made in 1 mmole/L in 0.1 mmol/L HCl stock solution and stored at −20° C. The solutions were diluted and used immediately. Sodium nitroprusside was made in 1 mmole/L in PSS instantly.

Data was presented as the arithmetic mean±standard deviation (SD), unless otherwise noted. Significant differences between various parameters were determined by use of parametric analysis of variance followed by the Student t-test. A probability of $p<0.05$ was considered to be indicative of a statistically significant difference.

Figure 2:
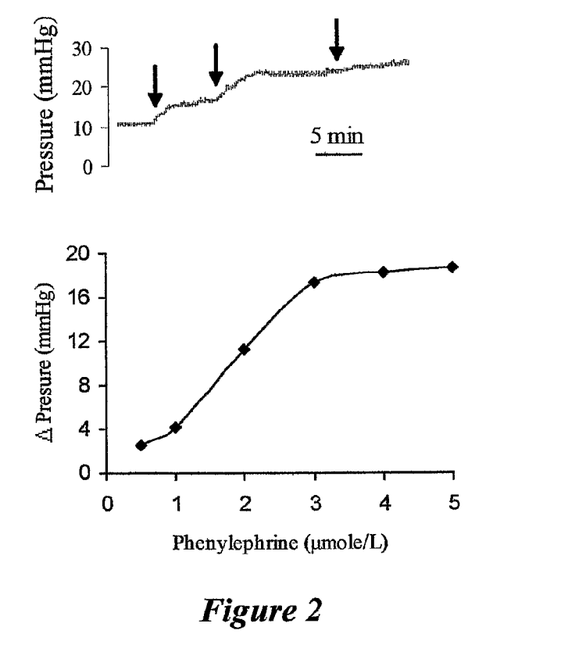
FIG. 2 shows an exemplary dosage-dependent myogenic response to phenylephrine.

The concentration-dependent contraction of the vessel 3 to phenylephrine is presented in FIG. 2. The pressure in vessel 3 increased sequentially when phenylephrine was administrated in increasing concentrations, as shown by the arrow points. The pressure reached a maximum when the concentration was 3 µmole/L as shown in FIG. 2. Dosage dependent vasodilation was observed by the administration of acetylcholine.

Figure 3:
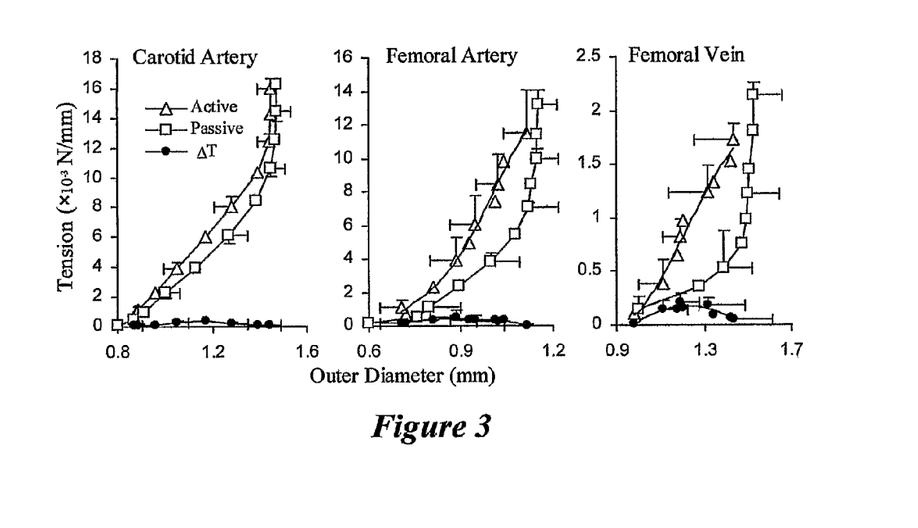
FIG. 3 shows tension-diameter relationships for passive and active properties of carotid artery and femoral artery and vein.

FIG. 3 shows tension-diameter relationships for passive and active properties of carotid artery and femoral artery and vein. In comparison with active response to phenylephrine, the passive tension was much smaller at the same diameter. Vasoconstriction caused a large contractile force in the vessel wall.

Figure 4:
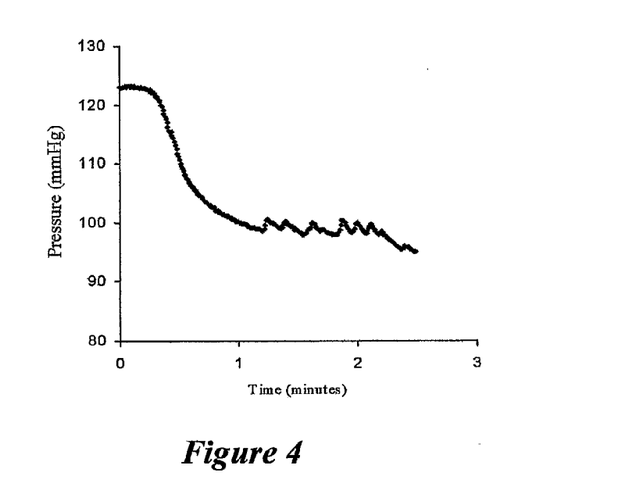
FIG. 4 shows a time course of pressure decrease during vasodilation with sodium nitroprusside (SNP).

FIG. 4 shows a time course of pressure decrease during vasodilation with SNP. There are spontaneous small amplitude contractions during the vasodilatory process. This phenomena has not been previously reported as it is unlikely that the diameter change is measurable with the pressure myograph for these small pressure changes.

The isovolumic myograph shown in FIG. 1 is just one exemplary embodiment of the present invention. Many other variations are possible and within the purview of the present invention. For example, the system shown in FIG. 5A is yet another exemplary embodiment of the present invention. This exemplary embodiment may be used for measuring isometric (FIG. 6) and isotonic vasomotion (FIG. 7) and is substantially similar to the exemplary embodiment shown in FIG. 1, but also includes a computer-controlled electronic pressure or volume regulator as well as computer controlled measurement of vessel diameter.

Figure 6:
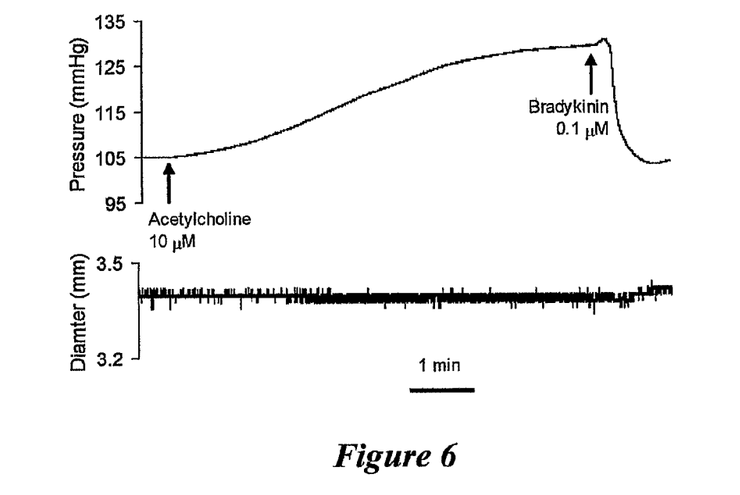
FIG. 6 shows an exemplary isometric experiment on a swine right coronary artery (RCA) reflecting a regulated pressure to maintain a constant diameter during vasomotion.
Figure 7:
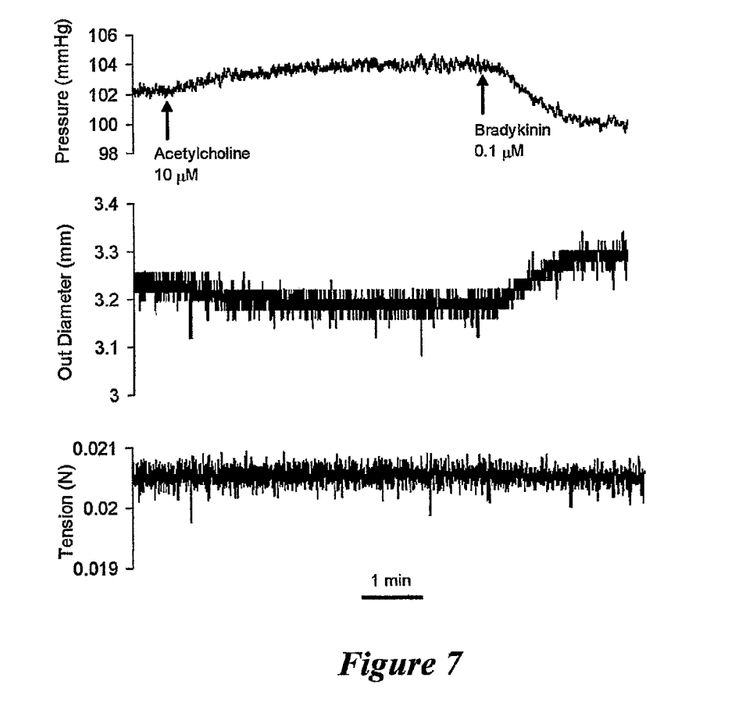
FIG. 7 shows an exemplary isotonic experiment on a swine right coronary artery (RCA) reflecting a regulated pressure to maintain a constant tension (product of pressure and diameter) during vasomotion.

This embodiment also addresses the limitations of conventional methods, namely, that although both isometric (constant length) and isotonic (constant tension) mechanical testing have been utilized extensively in skeletal muscle preparations to understand muscle mechanics, to date, no similar device that allows both isometric and isotonic experiments in cylindrical vessels has been created, let alone with electronic and/or computer control. The isovolumic method (constant volume) can be extended to isometric and isotonic modes as well, as described with respect to FIG. 5B and as shown in FIGS. 6 and 7, respectively.

Figure 5B:
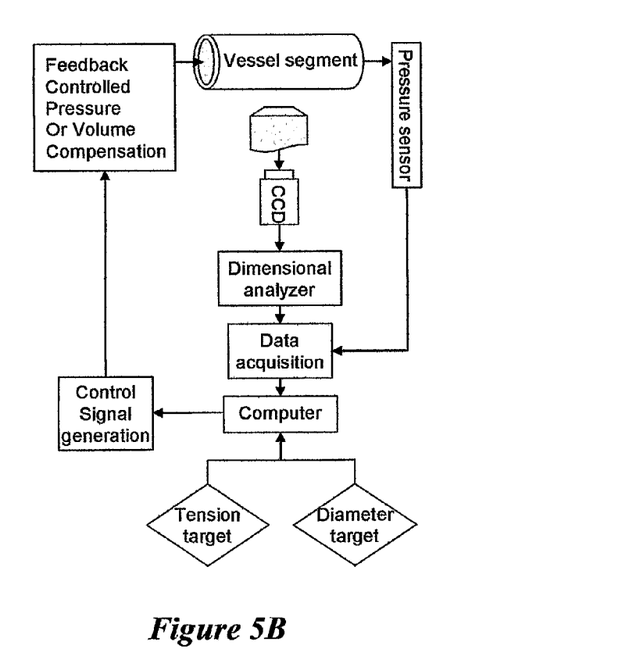
FIG. 5B shows a pressure or volume control feedback loop as used in exemplary embodiments of the present invention.

FIG. 5B shows a schematic feedback loop for the isometric and isotonic measurements used in the exemplary embodiment of FIG. 5A. To better understand the feedback loop control of this embodiment, first, isometric vasoactivity is considered. The diameter of vessel 3 will increase or decrease during relaxation or contraction, respectively. The isometric vasomotion requires that the vessel 3 diameter during vasoactivity is maintained constant by regulating the pressure or volume. Therefore, pressure or volume is regulated in a feedback loop to a set diameter. During vasoconstriction, the reference diameter is decreased. The system measures the decrease in diameter and responds by increasing the pressure or volume to the set value. The feedback loop is reiterated until the diameter is maintained within 1% of the set value. Conversely, pressure or volume is decreased during vasodilatation to decrease the diameter to the set value through a negative feedback loop as shown in FIG. 6.

Next, isotonic vasoactivity is considered. Isotonic vasomotion requires that circumferential tension of vessel 3 be constant (e.g., the product of pressure and inner radius is constant). During isotonic contraction, the circumferential tension is maintained constant but both pressure and diameter change as shown in FIG. 7. Briefly, the set point is computed as the product of pressure and diameter and the system will vary the pressure or volume to maintain a constant product similar to the isometric test.

In performing isometric and isotonic tests, the vessel diameter is measured. Typically, the smaller diameter of the vessel, the more transparent it is. Hence, the inner and outer diameters can be measured directly in smaller vessels. In the present system, the inner diameter can be continuously measured very well for vessels <600 µm in diameter. For vessels >600 µm in diameter, only the outer diameter can be measured directly. The inner diameter can be calculated from methods established in the art based on measurements of no-load cross-sectional area, axial stretch ratio and the incompressibility assumption. Hence, the inner diameter may be computed from the outer diameter and additional measurements as described above.

Figure 8:
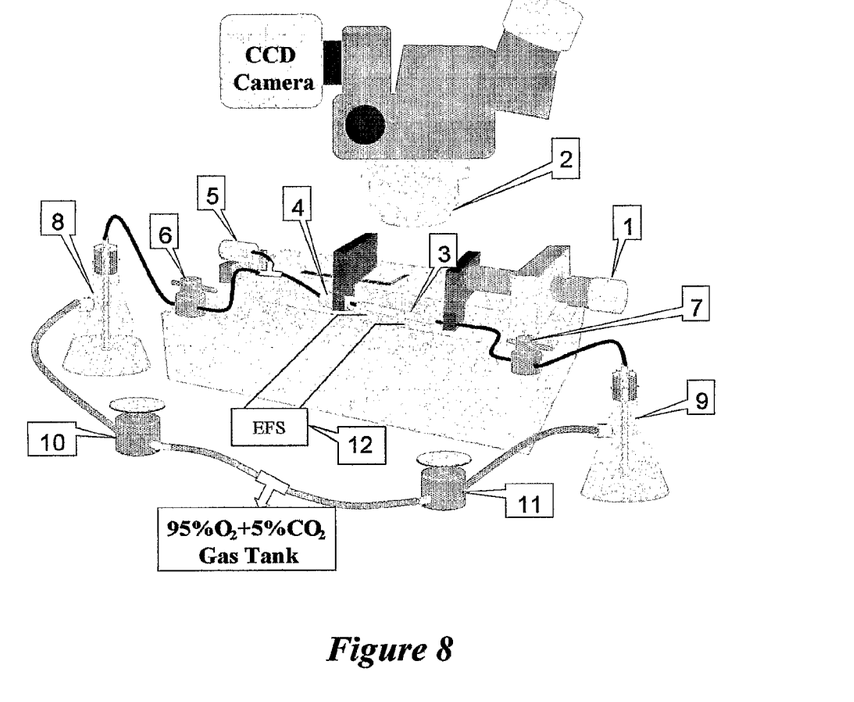
FIG. 8 shows an exemplary embodiment of the present invention as an isovolumic myograph having electrical stimulus and in the process of testing a blood vessel.

As discussed above, there are several modes of vessel smooth muscle activation, including, for example: (1) physical, such as increase in pressure during myogenic response, (2) chemical, such as with various agonist and antagonist through pharmacological agents and (3) electrical, through current stimulation. The first two are described elsewhere in this disclosure. The third type will be now discussed with respect to FIG. 8, which shows an arrangement where an electrical current source 12 can be used to stimulate the contraction of vessel by electrical field stimulation (EFS). A variety of electrodes may be used to provide such a stimulus. As a non-limiting example, two platinum wire electrodes are used to stimulate the vessel segment with an electronic stimulator by 20 Hz with square wave pulses of 0.3-ms duration and 60 mV. This embodiment can be used to show various vasoactivity in response to electrical stimulation.

Figure 9:
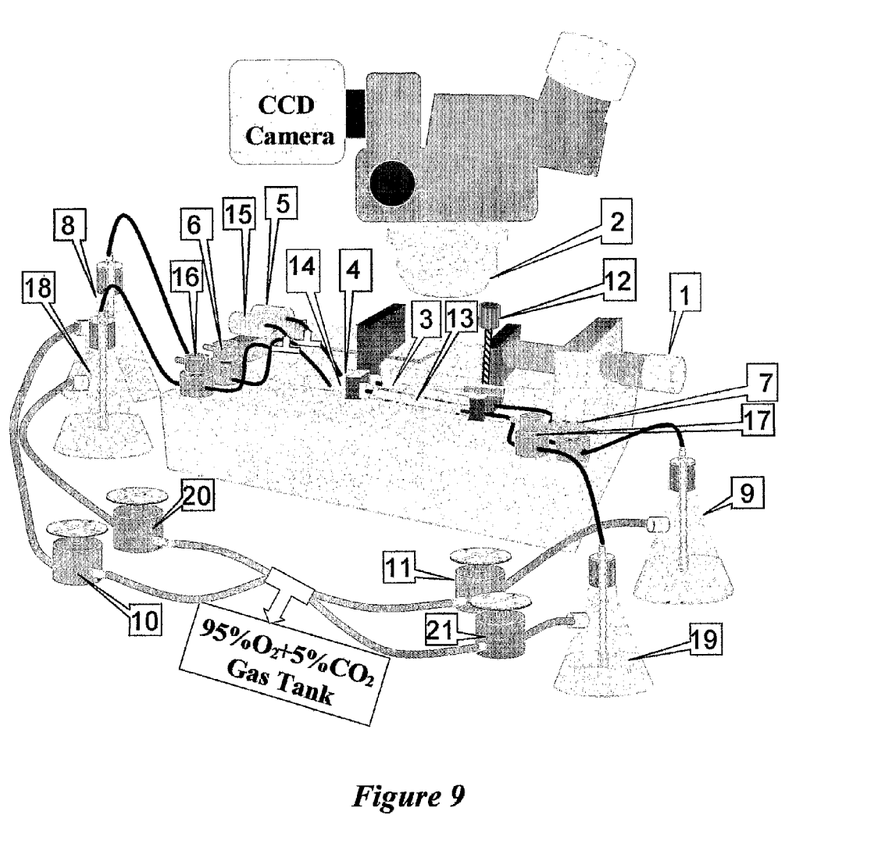
FIG. 9 shows an exemplary embodiment of the present invention as an isovolumic multi-vessel myograph.

FIG. 9 shows yet another exemplary embodiment according to the present invention wherein multiple vessels may be tested in the same system. In this particular example, a second blood vessel 13 may be simultaneously measured in the same organ bath as the first blood vessel 3. The tubing, force transducer 14 and pressure transducer 15, stopcocks 16 and 17, flasks 18 and 19, and fine pressure regulators 20 and 21 are similar to those used for the first blood vessel segment 3, and as described in the above exemplary embodiments. An additional manipulator 12 may be used to adjust the second blood vessel 13 length independently of the first blood vessel segment 3. The second blood vessel 13 may be exposed to the same vasostimulators or pressure loading as the first vessel 3. Using such a system, different vessels from different parts of the body may be tested for response to same or similar stimuli. Other uses are possible.

Figure 10A:
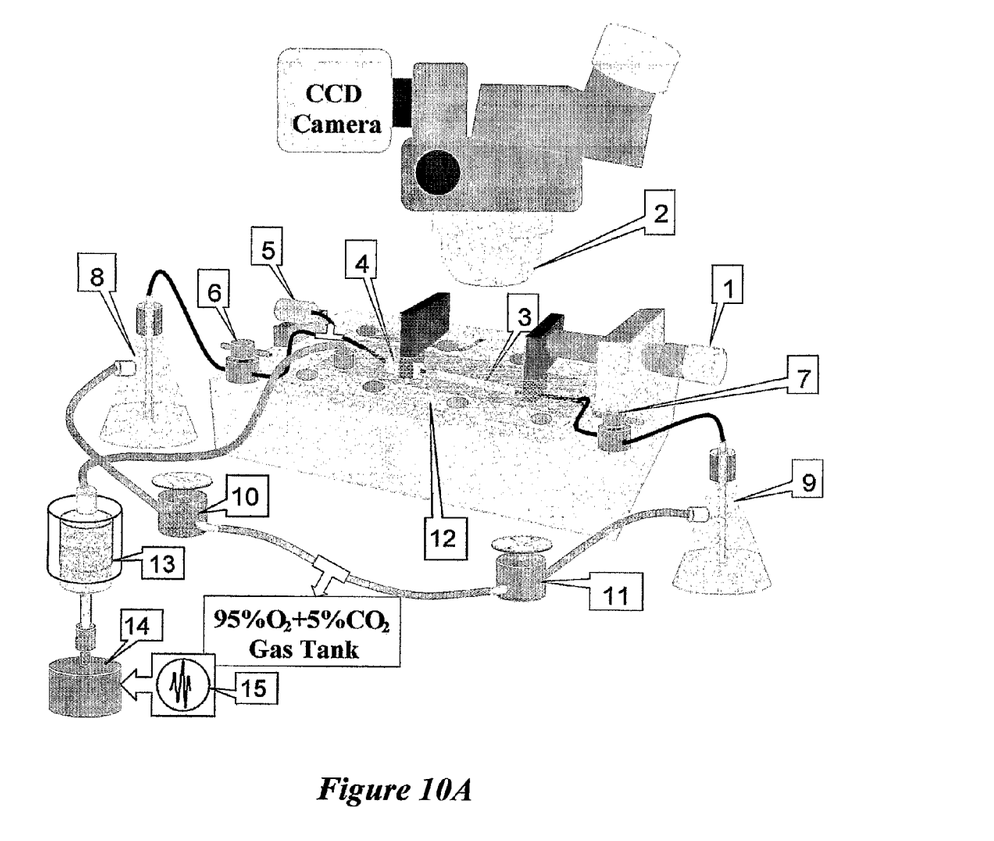
FIG. 10A shows an exemplary embodiment of the present invention as an isovolumic multi-pressure myograph.

In yet another exemplary embodiment, as shown in FIG. 10A, a system is presented that allows the testing of a blood vessel wherein the internal and external pressures of a blood vessel may be controlled. Further, a particular pulse pressure 15 may be electronically produced by pulse pressure generator 14 and forwarded to pressure transducer 13, leading to the sealed external bath 12 containing a blood vessel 3. The sealed external bath 12 is secured such that the external pressure of the blood vessel 3 is controllable by the pressure pulse system. This system allows an even more realistic model of the actual blood vessel environment that may be used to test a blood vessel as it experienced pulsatile pressure changes. Other tests and configurations are possible and within the scope of the present invention.

Figure 10B:
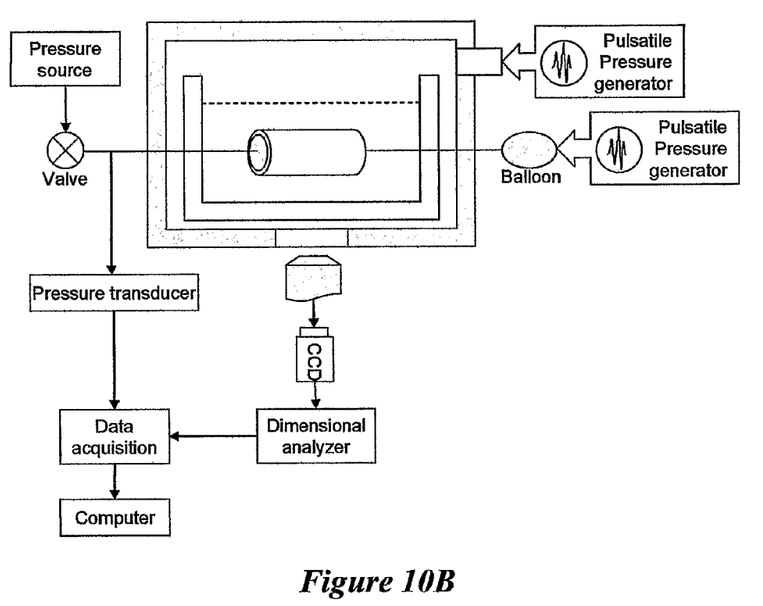
FIG. 10B shows a schematic perspective of an exemplary embodiment of the present invention having multiple pulsatile pressure controls.

In vivo, vessels experience pulsatile intravascular pressure conditions. Furthermore, some vasculatures such as the coronary vessels experience pulsatile external loading in addition to pulsatile intravascular loading. Hence, it is very useful to mimic both intravascular as well as external pulsatile loading conditions in an exemplary embodiment of the present invention, as shown in FIG. 10B. This embodiment shows a schematic of an isovolumic system that enables internal and external pulsatile pressure conditions. This can be readily done using the present invention by pressurizing the external medium (solution bath) of the vessel with a pulsatile pressure apparatus. To generate internal pulsatile pressures, a compliant balloon is connected in series with the vessel. The balloon is then loaded externally with a pulsatile pressure. The pressure pulse is transmitted to the lumen of the vessel through the compliant balloon.

Although the above examples show some of the advantages of the present invention, additional benefits and abilities are also inherent and apparent in the invention. For example, a myogenic response may be measured through a pressure response after a sudden change in pressure. Also, axial force measurements may be made allowing for measurement of simultaneous axial forces.

Yet another use of the present invention is for determining the filtration rate in small vessels. The filtration rate can be computed during an isovolumic experiment. Consider a vessel of cylindrical geometry whose volume is given by $$V = \frac{\pi}{4} D^2 L$$

A change in volume during an isovolumic contraction is due to filtration and can be related to the diameter change as follows:

$$\delta V = \frac{\pi}{2} DL \delta D$$

The filtration rate $J_V$ can be given as $$J_V = \frac{\delta V}{\delta t} = \frac{\pi}{2} DL \frac{\delta D}{\delta t}$$

The filtration rate per surface area, S, can be expressed as $$J_V/S = \frac{1}{2} \frac{\delta D}{\delta t}$$

Hence, the filtration rate is equal to one half of the rate of change of diameter which can be quantified during the experiment. These and other advantages of the present invention are evident to one having ordinary skill in the art after consideration of the present disclosure. All such advantages and uses are within the purview and scope of the present invention.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for determining the vasoactivity of a first blood vessel, the device comprising:
    a pair of conduits for positioning at either end of a blood vessel having a lumen, wherein each conduit in use forms a fluid seal with the lumen of the blood vessel;
    a pair of retaining walls that in use retain the blood vessel in a predetermined length, the pair of retaining walls configured to engage the pair of conduits;
    a first pressure transducer capable of measuring vasoactivity of the blood vessel, the first pressure transducer in communication with at least one of the conduits;
    a manipulator for changing a length of separation of the retaining walls to enhance the stretching or retracting of the blood vessel, wherein a fixed arm on the manipulator is used to hold a connector to one end of the blood vessel; and
    a pressure regulator in communication with a computer, the computer having a processor configured to adjust one of pressure or volume of a fluid within the blood vessel based upon data received from a detector configured to detect dimensional changes of the blood vessel;
    wherein the device is configured so that vasoactivity of the blood vessel can be determined by directly measuring pressure fluctuations in the lumen of the blood vessel through operation of the first pressure transducer while the blood vessel is maintained in the predetermined length by the pair of retaining walls, closed to flow conditions therethrough, and an isovolumic area is maintained within the lumen thereof.

2. The device of claim 1, wherein the device is configured to maintain the blood vessel in a fluid bath.

3. The device of claim 2, wherein the fluid bath contains an agonist to be tested on the blood vessel.

4. The device of claim 1, further comprising a source of fluid in communication with the lumen of the blood vessel, wherein the source of fluid contains an agonist to be tested on the blood vessel.

5. The device of claim 1, further comprising:
a second pair of conduits for positioning at either end of a second blood vessel having a lumen, wherein each such conduit in use forms a fluid seal with the lumen of the second blood vessel;
a second pair of retaining walls that in use retain the second blood vessel in a predetermined length, the second pair of retaining walls configured to engage the second pair of conduits;
a second pressure transducer capable of measuring vasoactivity of the second blood vessel, the second pressure transducer in communication with at least one of the second pair of conduits; and
a second manipulator for changing a length of separation of the retaining walls to enhance the stretching or retracting of the second blood vessel, wherein a fixed arm on the second manipulator is used to hold a connector to one end of the second blood vessel;
wherein the system is further configured so that vasoactivity of the second blood vessel as influenced by pressure fluctuations in the lumen of the second blood vessel is measurable by the second pressure transducer while the second blood vessel is maintained in the predetermined length by the pair of retaining walls and while the second blood vessel is closed to flow conditions therethrough and maintained in an isovolumic state.

6. The device of claim 1, further comprising a sealed housing for bathing and housing the blood vessel, wherein a pressure within the sealed housing is measurable by a second pressure transducer.

7. The device of claim 6, wherein the second pressure transducer measuring the pressure in the sealed housing is controlling a variable pulse pressure.

8. The device of claim 1, wherein the vasoactivity of the blood vessel is measurable by the first pressure transducer in response to an electrical stimulus.

9. The device of claim 1, wherein the device is configured to maintain the blood vessel under substantially isometric conditions.

10. The device of claim 1, wherein the device is configured to maintain the blood vessel under substantially isotonic conditions.

11. A system for determining the vasoactivity of a first blood vessel in reaction to a chemical, the system comprising:
a retaining device having a pair of conduits to form a fluid seal with a lumen of an excised blood vessel and a pair of retaining walls, configured to engage the pair of conduits, that retain the blood vessel in a predetermined length;
a chemical used to test the vasoactivity of the blood vessel;
a pressure transducer capable of measuring vasoactivity of the blood vessel, the pressure transducer in communication with the blood vessel;
a manipulator for changing a length of separation of the retaining walls to enhance the stretching or retracting of the blood vessel, wherein a fixed arm on the manipulator is used to hold a connector to one end of the blood vessel; and
a pressure regulator in communication with a computer, the computer having a processor configured to adjust one of pressure or volume of a fluid within the blood vessel based upon data received from a detector configured to detect dimensional changes of the blood vessel;
wherein the system is configured so that vasoactivity of the blood vessel in response to the chemical can be determined by directly measuring the pressure in the lumen of the blood vessel through operation of the first pressure transducer when the lumen of the blood vessel is closed to flow conditions, the blood vessel is maintained in an isometric state, and an isovolumic area is maintained in the lumen of the blood vessel.

12. The system of claim 11, wherein the system is configured to maintain the blood vessel in a fluid bath.

13. The system of claim 12, wherein the fluid bath contains the chemical to be tested on the blood vessel.

14. The system of claim 11, further comprising a source of fluid in communication with the lumen of the blood vessel, wherein the source of fluid contains the chemical to be tested on the blood vessel.

15. The system of claim 11, further comprising a microscope directed at the blood vessel to measure changes in wall thickness and diameter in response to stimulation.

16. The system of claim 11, further comprising a source of pressure in communication with the lumen of the blood vessel to maintain constant pressure of the lumen of the blood vessel.

17. The system of claim 11, further comprising a first pressure transducer in communication with the first blood vessel in a fluid bath and a second pressure transducer in communication with a second blood vessel contained in the fluid bath also containing the first blood vessel, wherein the first and second pressure transducers are configured to test the first blood vessel and the second blood vessel for vasoactivity.

18. The system of claim 11, further comprising a sealed housing for bathing and housing the blood vessel, wherein the pressure within the sealed housing is measurable by a pressure transducer.

19. The system of claim 18, wherein the pressure transducer measuring the pressure in the sealed housing is controlling a variable pulse pressure.

20. A method for measuring the vasoactivity of a blood vessel having a lumen in response to a chemical, the blood vessel having been excised and isolated from an animal body, the method comprising:
providing a system for determining the vasoactivity of a first blood vessel in reaction to a chemical, the system comprising:
a retaining device having a pair of conduits to form a fluid seal with a lumen of an excised blood vessel and a pair of retaining walls, configured to engage the pair of conduits, that retain the blood vessel in a predetermined length,
a chemical used to test the vasoactivity of the blood vessel,
a pressure transducer capable of measuring vasoactivity of the blood vessel, the pressure transducer in communication with the blood vessel,
a manipulator for changing a length of separation of the retaining walls to enhance the stretching or retracting of the blood vessel, wherein a fixed arm on the manipulator is used to hold a connector to one end of the blood vessel, and
a pressure regulator in communication with a computer, the computer having a processor configured to adjust one of pressure or volume of a fluid within the blood vessel based upon data received from a detector configured to detect dimensional changes of the blood vessel,
wherein the system is configured so that vasoactivity of the blood vessel in response to the chemical can be determined by directly measuring the pressure in the lumen of the blood vessel through operation of the pressure transducer when the lumen of the blood vessel is closed to flow conditions, the blood vessel is maintained in an isometric state, and an isovolumic area is maintained in the lumen of the blood vessel;
maintaining the blood vessel at a constant length;
maintaining the blood vessel at a constant internal volume; and
measuring pressure changes inside the lumen of the blood vessel using the pressure transducer after exposure of the blood vessel to the chemical.

21. The method of claim 20, wherein the chemical is exposed to the blood vessel through the lumen.

22. The method of claim 20, further applying an external pressure to the blood vessel.

23. The method of claim 22, wherein the applied external pressure is a variable pulse pressure.

24. The device of claim 5, wherein the device is configured to maintain the second blood vessel in a fluid bath also containing the first blood vessel.

* * * * *